US009222768B2

(12) United States Patent
Ernst et al.

(10) Patent No.: US 9,222,768 B2
(45) Date of Patent: Dec. 29, 2015

(54) SUPPLEMENTAL SCENE REFERENCE SURFACE DEVICES FOR THREE-DIMENSIONAL MAPPING

(76) Inventors: Maurice Moshe Ernst, Jerusalem (IL); Micha Geffen, Moshav Gillon (IL); Uri Raz, Tel Aviv (IL); Udi Cohen, Tel Adashim (IL); Uri Neta, Koranit (IL)

( * ) Notice: Subject to any disclaimer, the term of this patent is extended or adjusted under 35 U.S.C. 154(b) by 1067 days.

(21) Appl. No.: 12/665,747

(22) PCT Filed: Jun. 25, 2008

(86) PCT No.: PCT/IB2008/052528
§ 371 (c)(1),
(2), (4) Date: Dec. 21, 2009

(87) PCT Pub. No.: WO2009/001298
PCT Pub. Date: Dec. 31, 2008

(65) Prior Publication Data
US 2010/0179420 A1 Jul. 15, 2010

Related U.S. Application Data

(60) Provisional application No. 60/937,048, filed on Jun. 26, 2007.

(51) Int. Cl.
*G06K 9/00* (2006.01)
*G01B 11/24* (2006.01)
*G06T 7/00* (2006.01)
*A61B 5/00* (2006.01)
*A61B 19/00* (2006.01)
*A61C 9/00* (2006.01)

(52) U.S. Cl.
CPC .............. *G01B 11/24* (2013.01); *A61B 5/0073* (2013.01); *A61B 5/0088* (2013.01); *A61B 5/706* (2013.01); *G06T 7/004* (2013.01); *G06T 7/0042* (2013.01); *A61B 5/0084* (2013.01); *A61B 2019/505* (2013.01); *A61B 2019/5295* (2013.01); *A61C 9/004* (2013.01); *G06T 2207/30036* (2013.01)

(58) Field of Classification Search
USPC ................ 382/100, 128, 154; 433/25, 28, 33, 433/37–44, 50, 55, 68, 72–75, 140, 196, 433/215; 600/407, 414–417, 424–426, 429, 600/431, 476, 587, 590
See application file for complete search history.

(56) References Cited

U.S. PATENT DOCUMENTS

| 5,857,853 | A  | * | 1/1999  | van Nifterick et al. | .......... 433/68  |
| 6,108,497 | A  | * | 8/2000  | Nakayama et al. | ........... 348/140 |
| 6,648,640 | B2 | * | 11/2003 | Rubbert et al. | .................. 433/24  |
| 6,925,198 | B2 | * | 8/2005  | Scharlack et al. | ............ 382/128 |
| 8,491,306 | B2 | * | 7/2013  | Raby et al. | .................... 433/214 |

(Continued)

*Primary Examiner* — Eric Rush

(57) ABSTRACT

Supplemental reference surface devices are provided for use in three-dimensional modeling of intra-oral scenes using identifiable positional characteristics from structured illumination or other techniques. Reference surface devices having at least one substantially plane smooth non-polished face are disclosed for locating the positions of intra-oral features, and for stitching together separate 3D tiles according to the identifiable positional characteristics. Reference can be attached to an intra-oral feature in or adjacent to the imaged intra-oral scene. Disclosed are reference surface devices having orientation and position indicia, as well as reference surface devices having a multiplicity of faces distributed in spatial position and angular orientation to facilitate correlation of 2D images obtained by imaging systems in different positions.

24 Claims, 9 Drawing Sheets

(56) References Cited

U.S. PATENT DOCUMENTS

| | | | |
|---|---|---|---|
| 2002/0028418 A1* | 3/2002 | Farag et al. | 433/29 |
| 2003/0012423 A1* | 1/2003 | Boland et al. | 382/154 |
| 2003/0219148 A1 | 11/2003 | Scharlack et al. | |
| 2006/0072810 A1* | 4/2006 | Scharlack et al. | 382/154 |
| 2006/0083422 A1* | 4/2006 | Ernst et al. | 382/154 |
| 2006/0154198 A1* | 7/2006 | Durbin et al. | 433/215 |
| 2006/0212260 A1 | 9/2006 | Kopelman et al. | |

* cited by examiner

SUPPLEMENTAL SCENE REFERENCE SURFACE DEVICES FOR THREE-DIMENSIONAL MAPPING

CROSS REFERENCE TO RELATED APPLICATIONS

This application claims the benefit of priority to U.S. Patent Application Ser. No. 60/937,048, filed on Jun. 26, 2007, entitled "Supplemental Scene Reference Surfaces For Three-Dimensional Mapping" and incorporated herein in its entirety by reference.

FIELD OF THE INVENTION

The present invention relates to computerized modeling of three-dimensional objects, and, more particularly, to apparatus and methods for supplementing scenes with reference surface devices for improved model rendering.

BACKGROUND OF THE INVENTION

A common method of making a three-dimensional (herein also denoted as "3D") mathematical model of the surfaces of a scene is to project light reference patterns onto the scene, take an image of the scene showing the projected patterns (herein referred to as "structured illumination"), and then analyze the imaged patterns in comparison with an image of the same patterns projected onto a plane surface. By precisely measuring the respective displacements of the projected patterns in the image of the scene against the positions of the matching patterns in the reference image, it is possible to employ triangulation to determine the positions of the scene surfaces along the axis normal to the image plane, and thus obtain relative 3D positions of the scene surfaces for use in constructing a mathematical model of the scene surfaces. Both regular and random patterns are used in structured illumination.

It is noted that structured illumination is only one of several means of obtaining 3D information about intra-oral scenes. Other means include, but are not limited to: stereo optical imaging; and ultrasound. Various techniques are discussed and disclosed in U.S. Pat. No. 6,402,707 to one of the present inventors. Thus, the background and principles of the present invention are not limited to use in conjunction with structured illumination, but apply to other means of obtaining 3D information about intra-oral scenes, in general herein denoted as "imaging of an intra-oral scene". It is therefore understood that in the present application, structured illumination is used only as a non-limiting example to illustrate the application and use of embodiments of the present invention. Structured illumination is important in dental applications because of the ability to provide 3D models of intra-oral scenes with a minimal amount of equipment. The interior of the human mouth presents a relatively small cavity in which to insert imaging equipment, and the use of structured illumination, as described above, is well-suited to intra-oral use.

The term "intra-oral scene" herein denotes any collection of intra-oral objects, artifacts, surfaces, or features, which can be visualized and modeled, including, without limitation, both natural and artificial features. Three-dimensional models of intra-oral scenes support various aspects of dental practice.

It is also noted that the 2D image of a scene on which structured illumination patterns have been projected, and from which 3D position data can be derived, is in some sense equivalent to the 3D model which results therefrom through triangulation against the corresponding image of the patterns projected onto a plane surface, because the 3D model mathematically contains substantially the same 3D information as the 2D image correlated with the structured illumination. A similar correspondence exists for other 2D imaging techniques that result in 3D models (such as 2D stereo pairs). In this regard, 2D images containing 3D information, such as 2D images of the structured illumination, and the corresponding mathematical 3D models are, to some extent, interchangeable. Therefore, in the present application, references to a "2D image" of a scene and references to a "3D model" of the scene derived from the 2D image are understood to refer to similar data, the only difference being that the data points inherent in the 2D image of the scene are not processed, whereas the data points inherent in the corresponding 3D model have been processed. The term "2D imaging system" herein denotes the apparatus for capturing a 2D image of a scene, including, but not limited to those illuminated by patterns of structured illumination; and the term "3D imaging system" herein denotes a 2D imaging system in conjunction with apparatus for obtaining 3D information, including, but not limited to apparatus for projecting structured illumination patterns. The processing of 2D position data to obtain 3D positioning information, such as processing the data of structured illumination patterns, is well-known in the prior art and is considered herein as an inherent capability in a 3D imaging system.

A restriction in using the above-described structured illumination method, however, results from the fact that the projected light patterns have a two-dimensional (herein also denoted as "2D") extent over the scene surfaces. This is necessary in order to provide the capability of matching the light patterns with their corresponding patterns in the reference scene.

As a consequence, there are limitations in the 3D models of intra-oral scenes produced by such a method. In particular, the following limitations are noted:

Edge Imaging Limitations

FIG. 1 illustrates a view of a tooth 101 (conceptualized as a labial surface of a lower incisor) on which is projected a structured illumination pattern extending over an area 103. Area 103 exhibits a perimeter 103a and a center position 103b. Typically, in a normal projection onto a flat surface, area 103 has a square aspect ratio with a side length 103c denoted herein as "S". As described above, in order to achieve pattern matching, the structured illumination pattern requires a minimum 2D area, here shown as area 103. Center position 103b defines the x-y position of the pattern for modeling work. As a result, the effective portion of tooth 101 which can be modeled by using structured illumination in this fashion is denoted by a boundary 105, which is nominally a distance S/2 from the edge of tooth 101. This limitation is shown in FIG. 1 near an edge 113 of the tooth's occlusal surface. When projecting the structured illumination with the center 103b on boundary 105, such as in a location 107, the position can be accurately determined. When going outside boundary 105, however, such as in a location 109, a portion 111 of the structured illumination is lost, and thus the pattern may not be matchable with the corresponding pattern projected on the reference plane.

The distance s/2 from the edge is not a precisely-determined limit, because there may be cases where the pattern of the structured illumination can be matched over a smaller area. Conversely, if the structured illumination is not projected normally to the surface, the structured illumination will be distorted by a factor of $1/(\sin \alpha)$, where $\alpha$ is the incident angle of the projection. Thus, in cases where the incident angle is less than 90°, the boundary limit will be more than s/2 from the edge of the tooth.

Stitching Discontinuity Limitations 3D objects scenes generally cannot be visualized completely from a single direction, but must be visualized from a number of positions. That is, a 3D model typically must be constructed from the results of a set of separate imaging operations performed in different positions and/or in different directions, each of which results in an incomplete portion of a 3D model. Combining the separate 3D model portions (also referred to as "tiles") resulting from these separate operations is generally referred to as "stitching". In order to stitch together the separate 3D model tiles—that is, to stitch the incomplete 3D model tiles derived therefrom—and thereby obtain a unified 3D model, the different separate 3D models need to have a certain amount of overlapping or common features, by which the stitching regions can be identified. If the separate 3D model tiles do not have such common features, there is typically no way to stitch them together to obtain a unified 3D model.

FIG. 2 illustrates the stitching limitations resulting from using structured illumination for intra-oral 3D imaging. A tooth 201 (conceptualized as a lower incisor) is shown in side view, with a labial surface 203 and a lingual surface 205. A projection system (not shown) projects structured illumination patterns (not shown) onto the surfaces for imaging with imaging systems capable of capturing images of the structured illumination for comparison with the patterns against an image of those patterns on a reference surface device, as previously discussed.

An imaging system in a position 215 is capable of capturing 3D information of surface 203 in a region 207. An imaging system in a position 219 is capable of capturing 3D information of surface 205 in a region 209. However, because of the edge imaging and surface area limitations as discussed above, a region 211 and a region 213 adjacent to the edge of the tooth's occlusal surface cannot be satisfactorily imaged. Likewise, an imaging system in a position 217 is generally incapable of rendering any images in a region 221 connecting labial surface 203 with lingual surface 205. In such a case, there is no way to stitch the images produced by a 3D imaging system in position 215 with the images produced by a 3D imaging system in position 219. Thus, the use of structured illumination for intra-oral 3D imaging may result in discontinuities that make stitching difficult or impossible.

It is noted that the same imaging system may be used in different positions. Thus, in FIG. 2, the same imaging system may be sequentially used in positions 215, 217, and 219. It is the positions of the imaging system which are necessarily different for multiple 3D model imaging, rather than the imaging systems themselves. Similarly, the other figures of the present application relate to different imaging system positions, rather than different imaging systems themselves. Of course, separate imaging systems may also be employed for each different position without limitation in this regard.

Limitations in Imaging and Modeling of Special Features

Small objects and other special intra-oral features often lack sufficient surface area for satisfactory 3D reconstruction from projection of structured illumination patterns. Even if 3D reconstruction is achieved, there may be insufficient 3D area in the tile to enable stitching to another tile. In addition, if a feature has a polished or reflective surface, structured illumination patterns typically are not visible when projected onto such features.

This limitation is illustrated in FIG. 3, for an abutment 307, shown as being located in position for the placement of a crown to replace a missing lower incisor. Abutment 307 is affixed to an implant (not shown), and examples of abutment 307 include, but are not limited to: implant abutments; healing abutments; healing caps; and impression abutments. Teeth 301, 303, and 305 can be imaged using structured illumination, and their positions thus determined Abutment 307, however is considerably smaller than the teeth, and is comparable in size to area 103 for the projected patterns. In addition, abutment 307 may be reflective or otherwise not suitable for pattern projection. In this manner, structured illumination cannot be used to determine the precise position of abutment 307, and this is another limitation of the methodology.

Some attempts to overcome the imaging limitations of the prior art were described in U.S. Pat. No. 6,925,198, to Scharlack et al. '198' describes a method and system for creating three-dimensional models of implant-bearing dental arches, and other anatomical fields of view, employs three-dimensional scanning means to capture images of an anatomical field of view wherein there have been positioned (and preferably affixed to an anatomical feature) one or more three-dimensional recognition objects having a known geometry, such as a pyramid or a linked grouping of spheres. Image processing software is employed to locate and orient said recognition objects as reference data for stitching multiple images and thereby reconstructing the scanned field of view. Recognition objects placed in areas of low feature definition enhance the accuracy of three-dimensional modeling of such areas.

US Patent Application Publication No. 2008/0002869 to Scharlack et al., describes a three-dimensional-based modeling method and system designed for dentistry and related medical (and appropriate non-medical) applications. Data capture means produces a point cloud representing the three-dimensional surface of an object (e.g., dental arch). Three-dimensional recognition objects are provided, particularly within those areas in the image field that have low image definition, and particularly in such of these areas that appear in overlapping portions of at least two images, to provide the three-dimensional image processing software with position, angulation, and orientation information sufficient to enable highly accurate combining (or "stitching") of adjoining and overlapping images. Alignment, and creation of aligned related objects or models thereof, such as maxillar and mandibular arches, is facilitated.

There is thus a need for, and it would be highly-desirable to have, apparatus and methods for use in 3D modeling of intra-oral features in dental applications that overcome the aforementioned limitations of structured illumination and other means of 2D imaging. This goal is met by the present invention.

SUMMARY OF THE INVENTION

It is a goal of the present invention to extend the 3D modeling capabilities of imaging systems, such as those employing structured illumination. It is also a goal of the present invention to provide more accurate positioning information for imaging systems, including, but not limited to those employing structured illumination.

To attain these goals, embodiments of the present invention provides for supplemental reference surface devices to increase the richness of the intra-oral scene in a calibrated fashion that facilitates determining the precise 3D positions of intra-oral features and the stitching together of separate tiles by providing increased imaged area.

Embodiments of the present invention also facilitate determining the angulation and position of intra-oral features, such as abutments, teeth, false teeth and other prosthetic elements.

Therefore, according to the present invention there is provided a reference surface device for use with imaging of an intra-oral scene, the reference surface device including: (a) at least one substantially plane non-polished smooth face operative to providing an identifiable positional characteristic; and (b) a mounting point operative to attach to a feature having a substantially fixed location relative to the intra-oral scene; wherein the providing an identifiable positional characteristic is operative to provide information for determining the three-dimensional spatial position and orientation of the face relative to the intra-oral scene.

The reference surface device of the present invention allows for the stitching together of separate tiles of very small areas within the mouth, such as a single tooth, or an abutment. Additionally, the reference surface device may be used for imaging of the entire inner mouth.

In addition, according to the present invention there is provided a reference surface device including at least one orientation indicium having a predetermined position relative to the face; and at least one position indicium having a predetermined position relative to the face.

The reference surface device of the present invention may be used in conjunction, with an imaging system, such as the systems disclosed in WO2007/080563, to Ernst et al., incorporated herein by reference in its entirety.

Some embodiments of the present invention are directed to a system for three-dimensional modeling of the surface features of an intra-oral scene for a dental application, the system comprising:
  a. a reference surface device as described herein;
  b. a two-dimensional array of a plurality of random two-dimensional patterns;
  c. a storage medium for said array, said storage medium operative to allow projecting said array;
  d. a first image of said array projected on a reference surface
  e. a projector for projecting said array from said storage medium onto the intra-oral scene at a first angle;
  f. an acquiring means for acquiring a second image of said array projected on the intra-oral scene from a second angle;
  g. a first position calculator for calculating the two-dimensional relative positions of said random patterns based on the relative positions thereof in an image;
  h. a pattern-matching means for matching said random two-dimensional patterns in said first image with said random two-dimensional patterns in said second image;
  i. a parallax calculator for calculating the parallax between said random patterns in said first image with said random patterns in said second image;
  j. a second position calculator for calculating a three-dimensional relative positions of said random patterns based on said two-dimensional relative positions and said parallax; and
  k. a modeling means for constructing a three-dimensional model of the intra-oral scene based on said three-dimensional relative positions.

Some further embodiments of the present invention are directed to a system for three-dimensional modeling of the surface features of an intra-oral scene for a dental application, the system comprising
  a. a reference surface device as described herein;
  b. a two-dimensional array of a plurality of random one-dimensional patterns;
  c. a storage medium for said array, said storage medium operative to allow projecting said array;
  d. a first image of said array projected on a reference surface
  e. a projector for projecting said array from said storage medium onto the intra-oral scene at a first angle;
  f. an acquiring means for acquiring a second image of said array projected on the intra-oral scene from a second angle;
  g. a position calculator for calculating the two-dimensional relative positions of said random patterns based on the relative positions thereof in an image;
  h. a pattern-matching means for matching said random one-dimensional patterns in said first image with said random one-dimensional patterns in said second image;
  i. a parallax calculator for calculating the parallax between said random patterns in said first image with said random patterns in said second image;
  j. a position calculator for calculating a three-dimensional relative positions of said random patterns based on said two-dimensional relative positions and said parallax; and
  k. a modeling means for constructing a three-dimensional model of the intra-oral scene based on said three-dimensional relative positions.

Some embodiments of the present invention are directed to a system for real time intra-orally acquiring and registering three-dimensional measurements and images of intra-oral objects and features, where the intra-oral objects and features are located inside the oral cavity of a dental patient; the system including; a) a reference surface device as described herein; b) an intra-oral fixed global registration position inside the oral cavity of the dental patient, the intra-oral fixed global registration position is definable in terms of global coordinate space of the oral cavity, the global coordinate space is associated with a fixed global reference coordinate system, the global coordinate space includes a plurality of intra-oral local coordinate spaces in the oral cavity; c) a measuring and imaging device for measuring and imaging the intra-oral objects and features located in the oral cavity, relative to the same intra-oral fixed global registration position; and d) a mobile registration device for measuring and recording global positions and orientations of the measuring and imaging device, relative to the same intra-oral fixed global registration position.

Moreover, according to some embodiments of the present invention, there is provided a method for determining the position of an intra-oral feature, including: (a) providing a reference surface device; (b) attaching the reference surface device mounting point to the intra-oral feature; (c) imaging the intra-oral scene and the reference surface device face; (d) capturing a two-dimensional image of the intra-oral scene and the reference surface device face; (e) identifying the position and orientation indicia on the reference surface device face in the two-dimensional image; and (f) computing a three-dimensional position of the reference surface device mounting point as the position of the intra-oral feature.

Furthermore, according to some embodiments of the present invention, there is provided a method for producing a three-dimensional model of an intra-oral scene including: (a) providing a reference surface device; (b) positioning the reference surface device relative to the intra-oral scene; (c) attaching the mounting point to a feature having a substantially fixed location relative to the intra-oral scene; (d) imaging the intra-oral scene and the reference surface device, including at least one identifiable positional characteristic on the reference surface device; (e) capturing, from a first position, a first two-dimensional image of the intra-oral scene including the reference surface device and the at least one identifiable positional characteristic; (f) obtaining a first three-dimensional model from the first two-dimensional image; (g) capturing, from a second position, a second two-dimensional image of the intra-oral scene including the reference surface device; (h) obtaining a second three-dimensional model from the second two-dimensional image; and (i) stitching the first three-dimensional model to the second three-dimensional model according to the at least one identifiable positional characteristic.

There is therefore provided, in accordance with an embodiment of the invention, a reference device, including: a reference surface including at least one substantially plane non-polished smooth face operative to provide an identifiable positional characteristic; and a mounting element attached to the reference surface, the mounting element including a mounting point adapted to be attached to a feature having a substantially fixed location relative to the intra-oral scene;

the identifiable positional characteristic is at a predetermined spatial position from the mounting point for providing information for determining the three-dimensional spatial position and orientation of the face relative to the intra-oral scene.

In an embodiment, the reference surface includes a plurality of faces.

In an embodiment, the plurality of faces is spatially distributed.

In an embodiment, the plurality of faces is spatially distributed in at least two dimensions.

In an embodiment, the plurality of faces is spatially distributed in three dimensions.

In an embodiment, at least some of the faces are on a sector of at least one prism.

In an embodiment, at least one prism includes a plurality of the prisms.

In an embodiment, at least some of the faces are formed by a pyramidal depression of the faces on a sector of a prism.

In an embodiment, the plurality of faces comprises a plurality of prisms.

In an embodiment, the plurality of faces is further distributed in an angular orientation.

In an embodiment, the mounting point is in a predetermined angular orientation relative to the face.

In an embodiment, the reference surface device further includes at least one of:

an orientation indicium having a predetermined position relative to the face; and a position indicium having a predetermined position relative to the face.

In an embodiment, the reference surface device includes at least one orientation indicium and at least one position indicium.

In an embodiment, the reference surface device includes a plurality of orientation indicia and a plurality of position indicia.

There is also provided, in accordance with an embodiment of the invention, a system for real time intra-orally acquiring and registering three-dimensional measurements and images of intra-oral objects and features, the intra-oral objects and features are located inside the oral cavity of a dental patient; the system including:

a reference surface device;

a measuring and imaging device for measuring and imaging the intra-oral objects and features located in the oral cavity, relative to at least one identifiable positional characteristic of the reference surface device; and a mobile registration device for measuring and recording global positions and orientations of the measuring and imaging device, relative to the same intra-oral fixed global registration position.

In an embodiment, the measuring and imaging device is operative to provide structured illumination.

In an embodiment, the measuring and imaging device is further operative to provide the identifiable positional characteristic by a display of the structured illumination.

In an embodiment, the measuring and imaging device is operative to apply a visible pattern on the at least one substantially plane non-polished smooth face of the reference surface device.

There is additionally provided, in accordance with an embodiment of the invention, a method for determining the position of an intra-oral feature, including:

providing a reference surface device in a mouth of a patient so as to attach a reference surface device mounting point to the intra-oral feature;

imaging the intra-oral scene and the reference surface face thereby capturing a two-dimensional image of the intra-oral scene and the reference surface face; and identifying the position and orientation indicia on the reference surface device face in the two-dimensional image thereby determining a three-dimensional position of the mounting point as the position of the intra-oral feature.

In an embodiment, the imaging step includes providing structured illumination.

In an embodiment, the method further includes displaying the structured illumination so as to provide the identifiable positional characteristic.

In an embodiment, the imaging step further includes providing a cursor over the two-dimensional image.

In an embodiment, the method further includes locating the cursor over the two-dimensional image.

In an embodiment, the method further includes computing a three-dimensional position of the face from the two-dimensional image.

There is still additionally provided, in accordance with an embodiment of the invention, a method for producing a three-dimensional model of an intra-oral scene including:

providing a reference surface device;

positioning the reference surface device relative to the intra-oral scene;

attaching the mounting point to a feature having a substantially fixed location relative to the intra-oral scene;

imaging the intra-oral scene and the reference surface, including at least one identifiable positional characteristic on the reference surface;

capturing, from a first position, a first two-dimensional image of the intra-oral scene including the reference surface and the at least one identifiable positional characteristic;

obtaining a first three-dimensional model from the first two-dimensional image;

capturing, from a second position, a second two-dimensional image of the intra-oral scene including the reference surface;

obtaining a second three-dimensional model from the second two-dimensional image; and stitching the first three-dimensional model to the second three-dimensional model according to the at least one identifiable positional characteristic.

In an embodiment, at least one identifiable positional characteristic is a pattern of structured illumination.

In an embodiment, at least one identifiable positional characteristic is a visible pattern applied to the at least one face.

BRIEF DESCRIPTION OF THE DRAWINGS

The invention will now be described in connection with certain preferred embodiments with reference to the following illustrative figures so that it may be more fully understood.

With specific reference now to the figures in detail, it is stressed that the particulars shown are by way of example and for purposes of illustrative discussion of the preferred embodiments of the present invention only and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

DESCRIPTION OF THE PREFERRED EMBODIMENTS

The principles and operation of a method according to the present invention may be understood with reference to the drawings and the accompanying description.

Reference Surface Device for Locating the Position of an Intra-Oral Feature

In the detailed description, numerous specific details are set forth in order to provide a thorough understanding of the invention. However, it will be understood by those skilled in the art that these are specific embodiments and that the present invention may be practiced also in different ways that embody the characterizing features of the invention as described and claimed herein.

Figure 4:
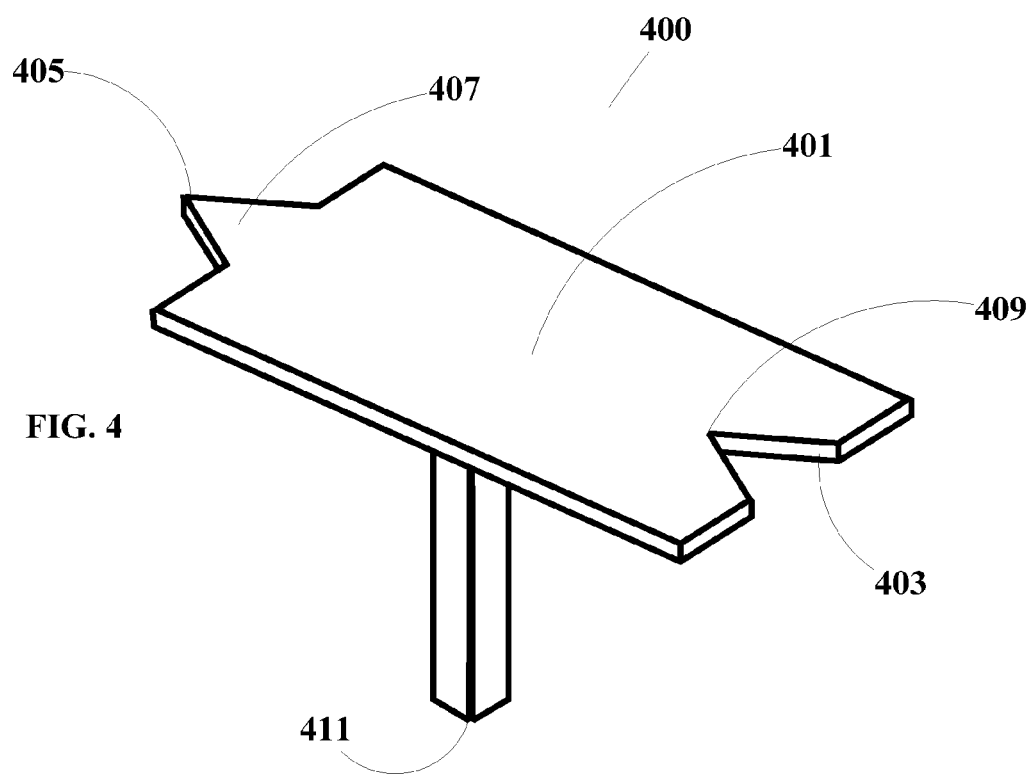
FIG. 4 shows a reference surface device according to an embodiment of the present invention, having position and orientation indicia.

FIG. 4 illustrates a reference surface device 400 according to an embodiment of the present invention, having position and orientation indicia, for precisely locating the position of an intra-oral feature. These indicia provide precise optical reference points for determining the location of a specific point in the intra-oral scene, such as a point on an intra-oral feature. The term "intra-oral feature" herein denotes any feature within the oral cavity having a substantially fixed location relative to an intra-oral scene, including, but not limited to: natural features, such as teeth, gums, and bone, and parts thereof; and artificial features, such as implants, abutments, prostheses, fixtures, appliances, and parts thereof. The term "substantially fixed location" in the context of an intra-oral scene herein denotes the position of a feature which remains in a fixed location relative to the intra-oral scene over a period of time necessary for satisfactory intra-oral 3D modeling. A normal, healthy tooth is a non-limiting example of a feature having a substantially fixed location in the context of an intra-oral scene of adjacent teeth. The tongue, lips, etc., however, are features which do not have a substantially fixed location.

In order to derive 3D information from 2D images, the 2D images typically must have at least one identifiable positional characteristic for use in making a triangulation measurement to determine 3D positional data. There are various prior art ways to provide identifiable positional characteristics, including, but not limited to:
  i. structured illumination, which, as previously discussed, provides identifiable positional characteristics via patterns of projected light;
  ii. stereo imaging, which provides identifiable positional characteristics by imaging identifiable positional characteristics that are inherent in the scene itself.

The term "pattern" herein denotes any visibly-identifiable characteristic in a scene or image.

According to an embodiment of the present invention, reference surface device 400 has a face 401 which is substantially plane, and with a non-polished smooth visible exterior. The reference surface device may be made out of any suitable rigid, inert, biocompatible material or combinations of such materials, such as, but not limited to, white plastic, aluminum or titanium.

The term "substantially plane" in the context of a face of a reference surface device herein denotes that the deviation from planarity of the face may be safely ignored in comparison with the depth resolution of the 3D imaging system. Having the face substantially plane is advantageous for projecting and utilizing the patterns of structured illumination. Reference surface devices according to embodiments of the present invention have at least one substantially plane non-polished smooth face whose geometrical extent is sufficient for displaying patterns of structured illumination and thereby provide information for determining the 3D spatial position and orientation thereof relative to the intra-oral scene; and the term "reference surface device" herein denotes a device or apparatus having at least these properties.

The term "non-polished smooth" herein denotes that the surface irregularities of the face are such that incident light rays thereupon are substantially scattered over a relatively large solid angle, but that the surface irregularities are not perceived on a macroscopic scale. That is, the surface irregularities are large compared to the wavelength of the incident light, but are small compared to the patterns of structured illumination projected thereon. The desired quality is that the face provides a suitable surface for the display of structured illumination patterns projected thereupon, visible from various angles, without coherently reflecting the incident light rays or causing visible distortion of the patterns.

In an embodiment of the present invention, the face is also prepared so that the minimum amount of visible light is absorbed thereby, the maximum amount being scattered from the face. In another embodiment, the face is uniformly scattering of all visible wavelengths. In a further embodiment, the face has a peak of scattering at a selected wavelength range corresponding to the wavelength range of the incident structured illumination.

In an embodiment of the present invention, a face has no inherent identifiable positional characteristic; an identifiable positional characteristic is provided by a pattern of structured illumination projected on the face.

According to further embodiments of the present invention, reference surface device 400 is positioned in the oral cavity such that the structured illumination projected onto the intra-oral scene is also projected onto face 401.

In another embodiment of the present invention, a face is provided with an inherent identifiable positional characteristic by applying a visible pattern on the face. Visible patterns are applied to the face by means including, but not limited to: printing; embossing; engraving; painting; etching; stamping; and molding. Reference surface devices according to this embodiment can be used with ordinary illumination and stereo imaging.

According to embodiments of the present invention, face 401 has at least one orientation indicium 403, and preferably a multiplicity of such orientation indicia, such as a second orientation indicium 407. Orientation indicium 403 is cut out from the face, whereas orientation indicium 407 protrudes from the face. The purpose of orientation indicia is to unambiguously identify the precise orientation of reference surface device 400 in an image thereof. In an embodiment of the present invention, the orientation indicia are geometrical characteristics of the boundary of a face, as shown in FIG. 4. A non-limiting shape for orientation indicia is triangular, as in cut-out orientation indicium 403, having an invisible baseline 413 on the perimeter of face 401 and whose apex 409 points to the interior of face 401. Solid orientation indicium 407 is also of a non-limiting triangular shape, with a baseline 415 on the perimeter of face 401, but whose apex 405 points away from face 401. Orientation indicia 403 and 407 are readily visible in an image and thereby establish an unambiguous orientation for reference surface device 400. Furthermore, apex 409 and apex 405 establish precise points for the 3D position and orientation of a line connecting them. Even if one or both of apex 409 and apex 405 are not visible in an image, the positions thereof can be precisely determined by extending the triangular boundaries of orientation indicia 403 and 407, respectively.

According to embodiments of the present invention, reference surface device 400 also includes a mounting point 411, whose 3D positions relative to face 401 and the orientation and position indicia thereof are predetermined and known. According to embodiments of the present invention, mounting point 411 includes provision for the attachment thereof to an intra-oral feature whose position within the intra-oral scene is to be determined, in such a manner as to physically support the face thereof in a substantially fixed position within the oral cavity relative to the intra-oral scene. Attachment means include, but are not limited to: screw fasteners; spring fasteners; clamps; wires; elastics; heat-shrink fasteners; friction fasteners; wrap fasteners; snap fasteners; fabric fasteners, including VELCRO; magnetic fasteners; mechanical fasteners; adhesives, tapes, glues, cements, epoxies, waxes, putties, plasters, and like materials; and combinations thereof. Procedures for making such attachments also include, but are not limited to physical processes, such as: increasing the roughness of a surface to facilitate adhesion; heating or cooling of a material matrix; hardening or softening of a material matrix; applying heat and/or pressure to a viscous material matrix; causing a phase change in a material matrix; and deforming, expanding, or contracting of a material.

In an embodiment of the present invention, the mounting point (such as mounting point 411) is located on an axis that is normal to a face of the reference surface device (such as face 401). In another embodiment, the axis is on the geometrical center of the face.

According to embodiments of the present invention, the dimensions of face 401 should be made as large as possible, while not interfering with viewing the intra-oral scene by the 2D imaging apparatus. In an embodiment of the present invention, the face is at least 2 mm wide and 2 mm long. In another embodiment of the present invention, the bases of orientation indicia 403 and 407 are nominally at least 0.33 mm in length.

Figure 8:
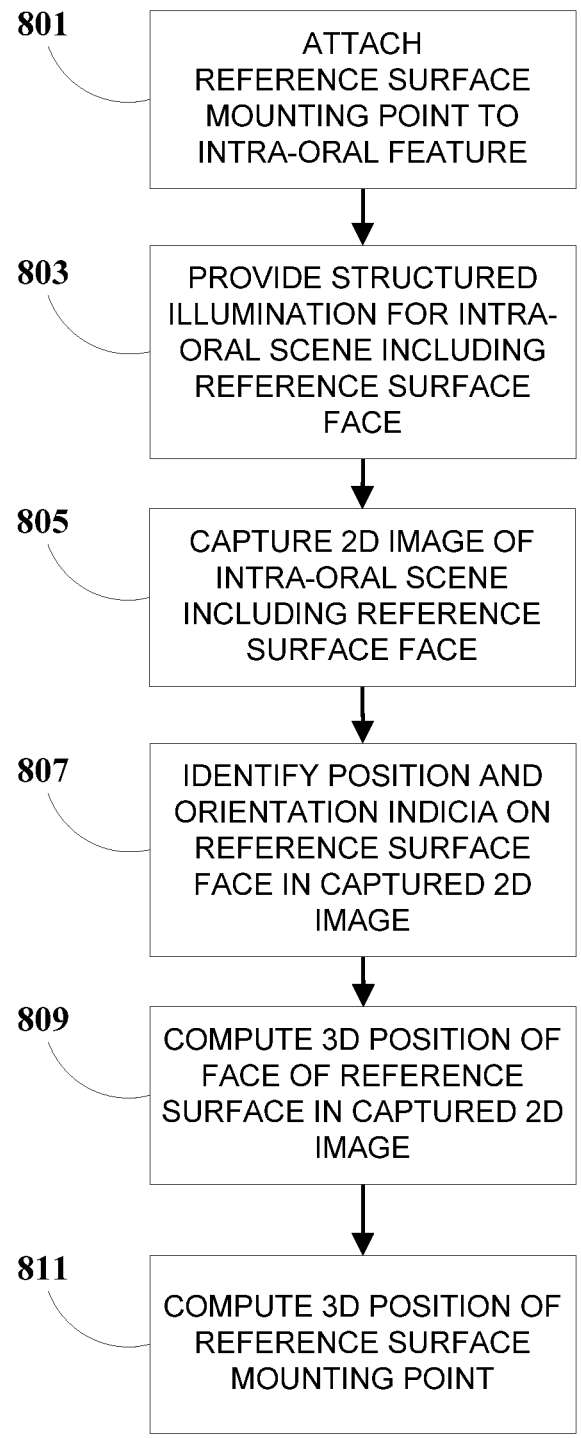
FIG. 8 is a flowchart of a method according to the present invention of using a reference surface device as in FIG. 4 to determine the position of an intra-oral feature.

Method of Determining Location of an Intra-Oral Feature using a Reference Surface Device According to an embodiment of the present invention, a method for the use of a reference surface device as shown in FIG. 4 is illustrated in FIG. 8. In a step 801, a reference surface device (such as reference surface device 400 in FIG. 4) is attached via the mounting point thereof (such as mounting point 411 in FIG. 4) to the intra-oral feature whose 3D position is to be determined. Attachment may be effected by any of the means previously discussed.

In a step 803, the intra-oral scene is provided with structured illumination projected in such a manner as to include at least one face of the reference surface device (such as face 401 in FIG. 4). In an embodiment of the present invention, the intra-oral scene also includes at least one additional fixed feature other than the intra-oral feature whose position is to be determined, and the structured illumination is also projected onto the additional fixed feature.

In a step 805, a 2D image of the intra-oral scene is captured, which includes the reference surface device. In an embodiment of the present invention, the captured 2D image also includes at least one additional fixed feature other than the intra-oral feature whose position is to be determined, as discussed above.

In an optional step 807, the position and orientation indicia (such as position indicia 405 and 409; and orientation indicia 407 and 403, respectively, in FIG. 4) of the reference surface device are identified. In an embodiment of the present invention, this identification is done automatically by software which analyzes the captured 2D image from step 805. In another embodiment of the present invention, this identification is done by an operator, such as at a computer, terminal, or console displaying the captured 2D image. Using a cursor, the operator identifies the position indicia (such as position indicia 405 and 409) by manually placing the cursor over each of the position indicia and indicating that the cursor is so placed, for example by pressing a key, clicking a pointing device button, or performing an equivalent action. In yet another embodiment of the present invention, the identification is done automatically by software and confirmed by an operator, who accepts the identification, for example by pressing a key, clicking a pointing device button, or performing an equivalent action. The terms "identify", "identifying", and various inflected forms thereof, in the context of position indicia, herein denotes not only indicating that a particular feature is a position indicium, but also determining the precise 2D location thereof in the 2D image.

In a step 809, the 3D position of at least one face of the reference surface device (such as face 401 in FIG. 4) within the intra-oral scene are computed, by triangulation on the patterns of structured illumination, using methods as known in the art, and by use of the known locations of the position indicia (such as position indicia 405 and 409), and by computing the angle of the reference face, likewise using the patterns of structured illumination as known in the art. The reference surface device of the present invention may be used in conjunction with suitable imaging systems, such as, but not limited to, those described in U.S. Pat. No. 6,402,707, issued to Ernst, incorporated herein in its entirety by reference.

The system used in conjunction with the reference may be constructed and configured for real time intra-orally acquiring and registering three-dimensional measurements and images of intra-oral objects and features, where the intra-oral objects and features are located inside the oral cavity of a dental patient. Such a system may comprise, for example: (a) an intra-oral fixed global registration position inside the oral cavity of the dental patient, the intra-oral fixed global registration position is definable in terms of global coordinate space of the oral cavity, the global coordinate space is associated with a fixed global reference coordinate system, the global coordinate space includes a plurality of intra-oral local coordinate spaces in the oral cavity; (b) a measuring and imaging device for measuring and imaging the intra-oral objects and features located in the oral cavity, relative to the same intra-oral fixed global registration position; and (c) a mobile registration device for measuring and recording global positions and orientations of the measuring and imaging device, relative to the same intra-oral fixed global registration position.

Aside from the positions of the indicia, 3D information about the reference surface device is not normally required.

In a step 811, the 3D position of the reference surface device mounting point (such as mounting point 411 in FIG. 4) in the intra-oral scene is computed from the known position of the mounting point relative to the reference face.

The mounting point is normally affixed to the intra-oral feature, whose position in the intra-oral scene is to be determined. It should be noted that the 3D position of the mounting point is determined in step 811, thereby the 3D position of the intra-oral feature is determined as being identical to that of the mounting point.

Figure 3:
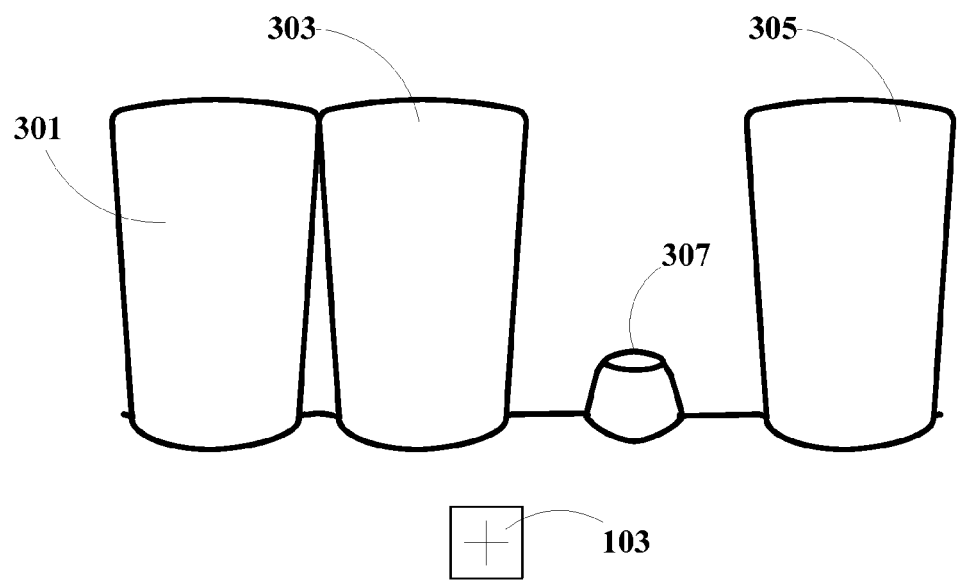
FIG. 3 shows prior-art limitations of using structured illumination to model the position of an abutment.

Using the apparatus shown in FIG. 4 and the method illustrated in FIG. 8, both of which are detailed above, it is possible, in a non-limiting example, to determine the position of abutment 307 shown in FIG. 3, whereas, as detailed previously, the use of prior-art methods employing structured illumination alone are inferior and unsatisfactory.

It is noted that, according to embodiments of the present invention, it is not necessary to directly determine the position of an intra-oral feature in the intra-oral scene. It is sufficient to obtain data using the methods of the present invention relating to the face of the reference surface device and the various indicia thereof, in the intra-oral scene, and for the mounting point of the reference surface device to be affixed to the intra-oral feature, as detailed above.

Reference Surface Device for Correlating Multiple 3D Models

Figure 1:
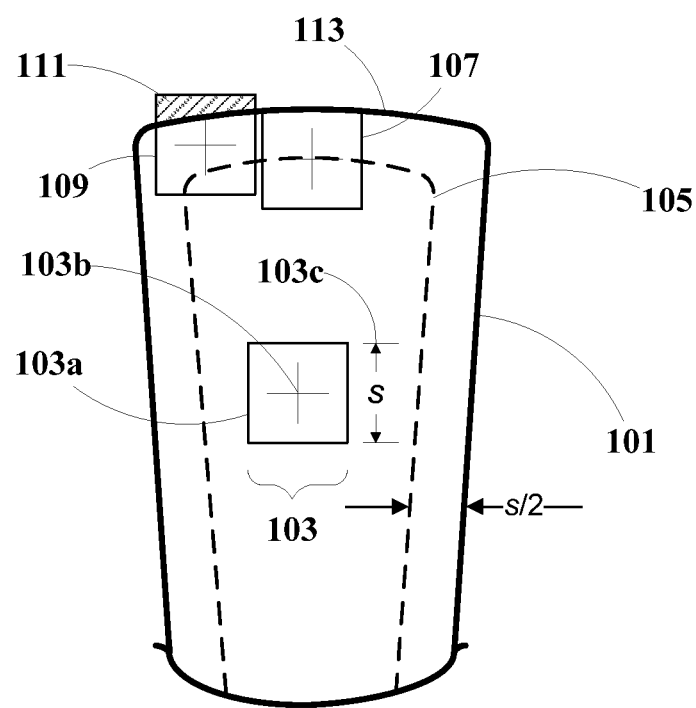
FIG. 1 shows a front view of a tooth with prior-art limiting boundaries for structured illumination.
Figure 2:
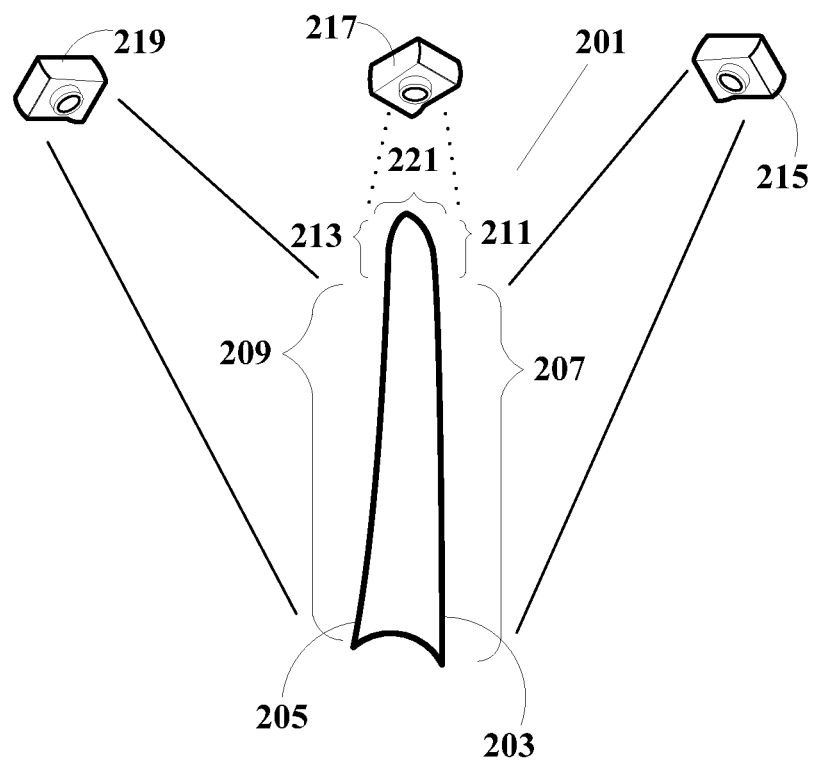
FIG. 2 shows a side view of a tooth showing prior-art limitations of stitching discontinuity from front imaging to back imaging.

Some additional embodiments of the present invention provide for a reference surface device with a multiplicity of substantially plane smooth non-polished faces which are distributed in position and in angular orientation. Such a configuration is advantageous for capturing 2D images of the same intra-oral scene from different positions in the oral cavity, and thus is advantageous for correlating different 2D images of structured illumination, and thereby stitching the different images together, in effect correlating different 3D models of the same intra-oral scene. FIG. 2 and the previous discussion thereof illustrate the limitations in the prior art which the present invention overcomes. Reference surface devices according to embodiments of the present invention may thereby be used to correlate multiple 3D models otherwise lacking common data, as illustrated in FIG. 2 and discussed previously.

In an embodiment of the present invention, the reference surface device faces are spatially distributed in two dimensions. In another embodiment of the present invention, the reference surface device faces are spatially distributed in three dimensions.

In another embodiment of the present invention, the multiplicity of faces includes faces which are geometrically similar. In a further embodiment of the present invention, the multiplicity of faces includes faces which are geometrically congruent. In still another embodiment of the present invention, the multiplicity of faces includes faces which are distributed uniformly in position. In yet a further embodiment of the present invention, the multiplicity of faces includes faces which are distributed uniformly in angular orientation.

Figure 5:
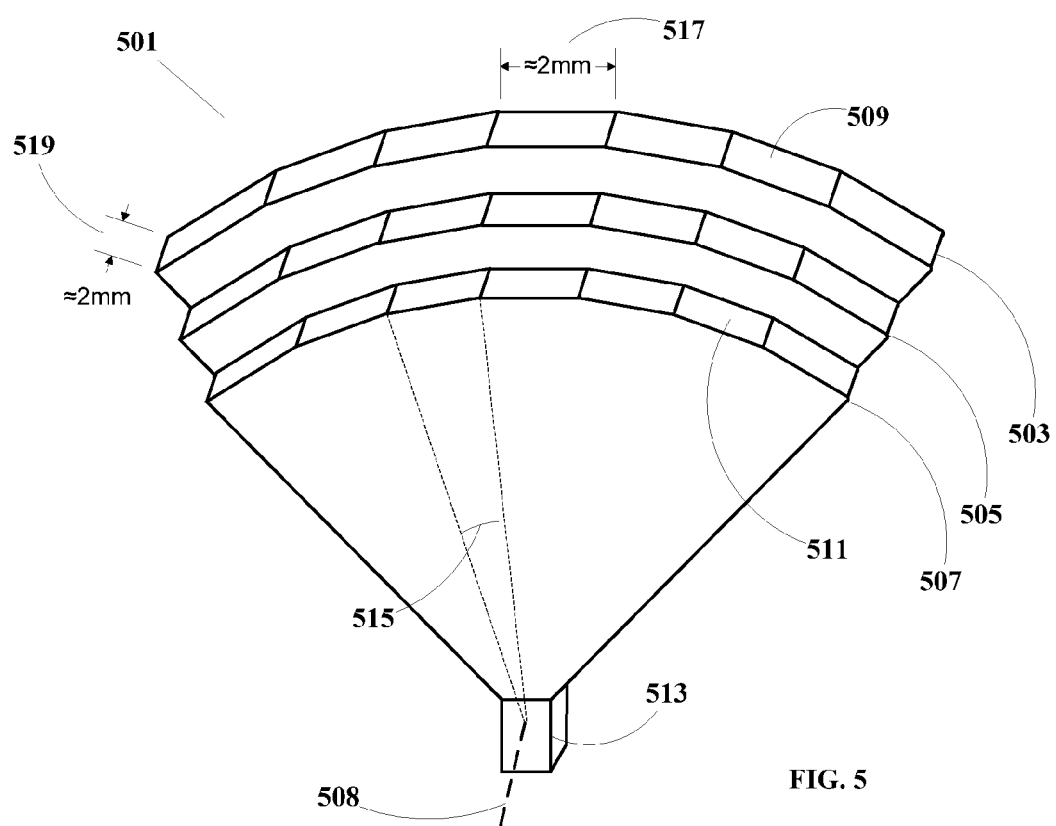
FIG. 5 shows a compound reference surface device according to an embodiment of the present invention, having a multiplicity of angularly-distributed reference faces.

FIG. 5 illustrates a reference surface device 501 according to an embodiment of the present invention, for correlating multiple intra-oral scenes, to enhance and facilitate the stitching of those scenes.

Reference surface device 501 features a multiplicity of substantially plane smooth non-polished faces, such as a face 509 and a face 511, which are uniformly distributed in spatial position (in three dimensions) and in angular orientation. In an embodiment of the present invention as illustrated in FIG. 5, the faces are on a multiplicity of sectors, shown as a sector 503, a sector 505, and a sector 507, each of which is a sector of a respective prism on a common axis 508, and each of which has a different nominal radius (not shown). The term "prism" is herein used in the geometric sense, as a polyhedron having two parallel polygonal faces joined by parallelogram faces. In an embodiment of the present invention, the full prisms (not merely the sectors thereof) have parallel faces each of which is a regular polygon of 36 sides, such that an angle 515 is 10°, so that sectors 503, 505, and 507 each subtend a total angle of 70°. This, along with other specific properties of this particular embodiment, is non-limiting; in other embodiments of the present invention, sectors subtend different angles. In an embodiment of the present invention, a face has a typical nominal length 517 of approximately 2 mm, and a typical nominal thickness 519 of approximately 2 mm; the precise lengths and thicknesses of the faces depend on the radius and thickness of the respective sector in which the face is located. In a further embodiment of the present invention, sectors 503, 505, and 507 each have a thickness of 2 mm. In this embodiment, the thickness of each face is thus 2 mm. The lengths of the sectors vary as follows: length of the faces of sector 503 is 2.106 mm; length of the faces of sector 505 is 2.053 mm; and the length of the faces of sector 507 is 2.000 mm. These sizes have been chosen for optimal resolution of structured illumination patterns while maintaining suitable distributions of faces in spatial location and angular position. The overall thickness of reference surface device 501 is thus 6.0 mm. In other embodiments of the present invention, the thickness of each sector is increased to 2.5 mm and 3.0 mm, respectively, making the total thickness of the reference surface device 7.5 mm and 9.0 mm, respectively.

Reference surface device 501 includes a mounting point 513, which may be attached to an intra-oral feature in the same manner as previously described.

Figure 6A:
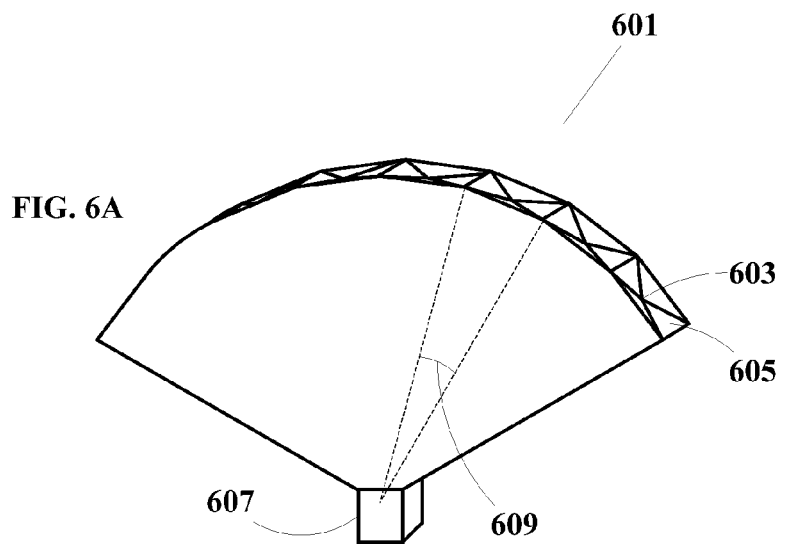
FIG. 6A shows a reference surface device according to another embodiment of the present invention, having a multiplicity of angularly-distributed reference faces.

FIG. 6A illustrates a reference surface device 601 according to an embodiment of the present invention, for correlating multiple intra-oral scenes, to enhance and facilitate the stitching of those scenes. Reference surface device 601 is a segment of a prism. The full prism from which this segment is taken has two parallel faces which are regular polygons of 24 sides, such that an angle 609 subtended from the axis of the prism is 15°. Each outer face of the prism sector is indented in a pyramidal configuration 603, having a typical face 605 at a shallow angle depressed by approximately 10°. In an embodiment of the present invention, the pyramidal depressions are oriented such that the edges of face 605 are oriented along the diagonals of the original (non-indented) prism face. In other embodiments of the present invention (not illustrated), the depressions are oriented along the bisectors of the original (non-indented) prism face.

Reference surface device 601 includes a mounting point 607, which may be attached to an intra-oral feature in the same manner as previously described.

Figure 6B:
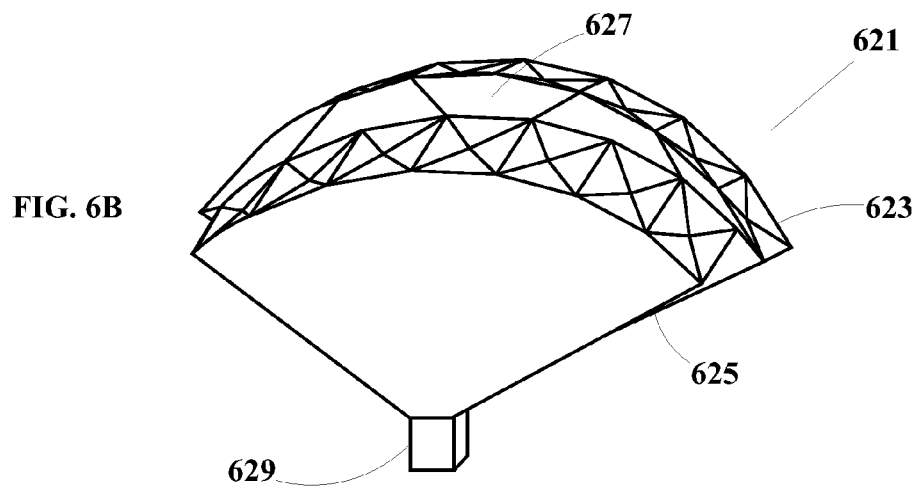
FIG. 6B shows a compound reference surface device according to yet another embodiment of the present invention, having angularly-displaced reference surface devices of the configuration shown in FIG. 6A.

FIG. 6B illustrates a reference surface device 621 according to an embodiment of the present invention, for correlating multiple intra-oral scenes, to enhance and facilitate the stitching of those scenes. Reference surface device 621 includes a multiplicity of reference surface devices similar to that which is illustrated in FIG. 6A, and which are of varying sector sizes and angular orientations. In FIG. 6B, reference surface device 621 is shown having two such sectors: a larger sector 623 subtending an angle of 120°, and a smaller sector 625 subtending an angle of 105°. In this embodiment, both sector 623 and 625 have the same radius. Sector 625 is displaced from sector 623 by a small angle (that is, the full prisms of sectors 623 and 625 are not parallel, but have axes that intersect at the displacement angle). The space between the outer reference faces of sectors 623 and 625 is filled with reference faces which are approximately trapezoidal in shape, such as a face 627.

Reference surface device 621 includes a mounting point 629, which may be attached to an intra-oral feature in the same manner as previously described.

Method of Correlating 3D Models

Reference surface devices as provided by embodiments of the present invention may be used advantageously to correlate 3D models of intra-oral scenes in a manner which overcomes the prior-art limitations previously discussed.

Figure 7:
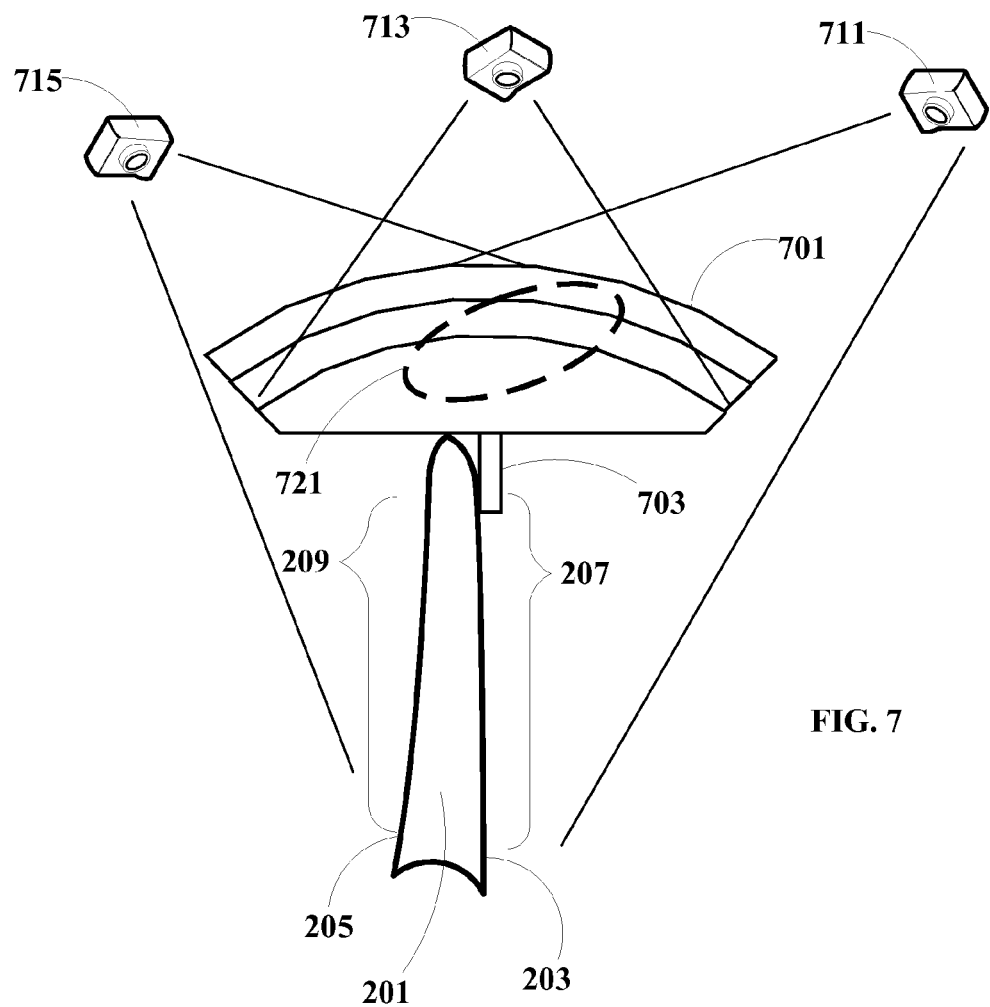
FIG. 7 illustrates a non-limiting use of a reference surface device to provide stitching continuity for multiple images of an intra-oral scene, according to an embodiment of the present invention.

FIG. 7 illustrates a non-limiting use of a reference surface device 701 to provide stitching continuity for multiple images of an intra-oral scene, according to an embodiment of the present invention.

Reference surface device 701 is of a configuration according to an embodiment of the present invention, similar to reference surface device 501 as previously discussed and illustrated in FIG. 5. In the embodiment illustrated in FIG. 7 for reference surface device 701, however, the sector is truncated by removing the apex at axis 508 (FIG. 5). The multiplicity of faces (such as face 509 and face 511) provide the essential portion for reference surface device 501, and thus the bulk of the volume of reference surface device 501 is not necessary. Hence, in the embodiment shown in FIG. 7, most of this excess volume is removed, so that reference surface device 701 can be placed more conveniently in the oral cavity, in proximity to the intra-oral scene of interest. FIG. 7 illustrates tooth 201 having labial surface 203 and lingual surface 205, as previously shown. As before, region 207 and region 209 are the areas which may be imaged for 3D modeling, as previously detailed.

In FIG. 2 and the description thereof, it is seen that in prior-art applications, there is insufficient correlation between a 2D image of labial surface 203 and a 2D image of lingual surface 205 to stitch the images together for a unified 3D model. FIG. 7, however, illustrates how the use of a reference surface device according to embodiments of the present invention overcomes this limitation.

Reference surface device 701 is placed within the oral cavity such that mounting point 703 is affixed to a nearby intra-oral feature, such as a tooth adjacent to tooth 201. In an embodiment of the present invention, mounting point 703 is not affixed to tooth 201 itself, in order that there be a clear view of tooth 201 by the imaging systems (discussed below). Thus, according to this preferred embodiment, reference surface device 701 is in a different plane from tooth 201, and the attachment is to a different tooth (not shown).

A projection system (not shown) projects structured illumination patterns onto the intra-oral scene and reference surface device 701. An imaging system in a position 711 is capable of capturing a 2D image from which can be derived 3D position data of labial surface 203 in region 207, and also 3D position data of the faces of reference surface device 701. An imaging system in a position 713 is not capable of capturing a 2D image from which 3D position data of the occlusal surface of tooth 201 can be derived (as previously described), but is capable of capturing a 2D image from which 3D data on of the faces of reference surface device 701 can be derived. An imaging system in a position 715 is capable of capturing a 2D image from which 3D position data of lingual surface 205 in region 209 can be derived, as well as 3D position data of the faces of reference surface device 701. It is noted that images captured by imaging systems in positions 711, 713, and 715 all capture 2D images from which may be obtained 3D position data of the faces of reference surface device 701, particularly within a region 721. Therefore, by using a reference surface device according to embodiments of the present invention, it is always possible:

a) to obtain a single 2D image of an intra-oral scene and to define therefrom 3D position data for correlation and efficient stitching; and b) multiple 2D images of an intra-oral scene which are sufficient to obtain 3D position data for correlation and efficient stitching, regardless of the limitations of the objects in the intra-oral scene themselves.

Figure 9:
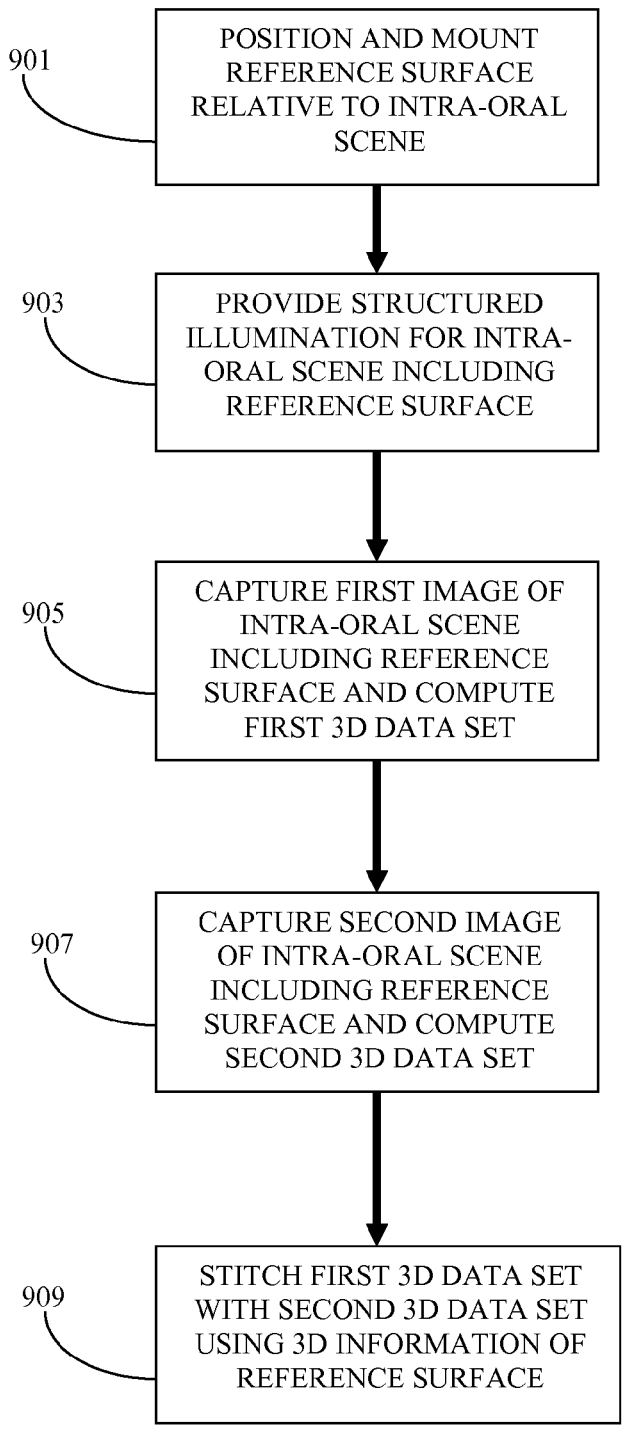
FIG. 9 is a flowchart of a method according to an embodiment of the present invention, for obtaining multiple images of an intra-oral scene and for stitching the multiple images together.

FIG. 9 is a flowchart of a method according to an embodiment of the present invention, for obtaining multiple images of an intra-oral scene and for stitching the multiple images together. In a step 901, a reference surface device according to the present invention (a non-limiting example of which is reference surface device 701 in FIG. 7) is positioned in a suitable location relative to the intra-oral scene to be modeled and mounted by affixation to an intra-oral feature. In a step 903, structured illumination is provided by projecting patterns of structured illumination onto the intra-oral scene such that patterns thereof are also projected onto the faces of the reference surface device. In a step 905, a first 2D image of the intra-oral scene, including the reference surface device, is captured and may be converted into a 3D data set. In a step 907, a second 2D image of the intra-oral scene, including the reference surface device, is captured from a different position than that used to capture the first 2D image, which then may be converted into another 3D data set. In a step 909, the first 2D image converted into a 3D data set is stitched with the second 2D image, converted into a 3D data set. Based on the 3D information available from the reference surface device, it is possible to stitch the first and second 3D data sets together, thereby overcoming limitations in the prior art, as illustrated in FIG. 2 and discussed previously.

It is noted that when a reference surface device is used in the method illustrated in FIG. 9, it is not necessary for the mounting point to be in a predetermined position or angular orientation relative to the faces, because the precise location of the mounting point is not used in the computations for stitching the 2D images together.

The references cited herein teach many principles that are applicable to the present invention. Therefore the full contents of these publications are incorporated by reference herein where appropriate for teachings of additional or alternative details, features and/or technical background.

It is to be understood that the invention is not limited in its application to the details set forth in the description contained herein or illustrated in the drawings. The invention is capable of other embodiments and of being practiced and carried out in various ways. Those skilled in the art will readily appreciate that various modifications and changes can be applied to the embodiments of the invention as hereinbefore described without departing from its scope, defined in and by the appended claims.

The invention claimed is:

1. A reference surface device for use with imaging of an intra-oral scene, the reference surface device comprising:
   a) at least one sector including a length defining a first end of said at least one sector, a plurality of faces, each face of said plurality of faces at an angular orientation with respect to each adjacent face, the plurality of faces extending along the length of the at least one sector, the at least one sector including oppositely disposed edges which extend from the edges of the outermost faces to a second end of said at least one sector, and wherein said plurality of faces is configured to provide at least one fully intraoral reference surface operative to provide an identifiable positional characteristic; and,
   b) a mounting element in communication with said second end of said at least one sector, wherein said identifiable positional characteristic is at a predetermined three-dimensional spatial position from a mounting point adapted to be attached to a feature having a substantially fixed location relative to said intra-oral scene, said intra-oral scene being configured to provide information for determining the three-dimensional spatial position and orientation of a face on said reference surface device relative to the intra-oral scene.

2. A reference surface device according to claim 1, wherein said reference surface device comprises at least one prism including said at least one sector, and wherein each face of said plurality of faces includes a pyramidal depression.

3. A reference surface device according to claim 2, wherein said at least one prism comprises a plurality of prisms.

4. A reference surface device according to claim 1, wherein said mounting element comprises a mounting point adapted to be attached to a feature having a substantially-fixed immobile location relative to the intra-oral scene.

5. A reference surface device according to claim 1, wherein said reference surface device comprises at least one substantially planar non-polished smooth face.

6. A reference surface device according to claim 1, wherein said mounting element is fixed to said second end of said at least one sector.

7. A reference surface device of claim 1, wherein said plurality of faces are spatially distributed in at least one of: two-dimensions or three-dimensions.

8. A reference surface device according to claim 1, wherein said mounting point is in a predetermined angular orientation relative to at least one of said plurality of faces.

9. A reference surface device according to claim 1, wherein said reference surface device is configured for use in a system for three-dimensional modeling of surface features of an intra-oral scene for a dental application.

10. A reference surface device according to claim 1, wherein each said at least one sector is on a common axis.

11. A reference surface device according to claim 1, further comprising at least one of:
   i) an orientation indicium having a predetermined position relative to said plurality of faces; and
   ii) a position indicium having a predetermined position relative to said plurality of faces.

12. A reference surface device according to claim 11, comprising at least one orientation indicium and at least one position indicium.

13. A reference surface device according to claim 12, comprising a plurality of orientation indicia and a plurality of position indicia.

14. A reference surface device according to claim 1, wherein said at least one sector includes at least one prism, wherein at least two of said plurality of faces are uniformly distributed in a spatial position.

15. A reference surface device according to claim 1, wherein said plurality of faces are distributed asymmetrically in position.

16. The reference surface device according to claim 1, wherein said length defining the first end of said at least one sector includes an arc.

17. The reference surface device according to claim 1, wherein said oppositely disposed edges taper inward from the first end to the second end.

18. A method for determining a position of an intra-oral feature in an intra-oral scene, comprising:
   a) introducing a reference surface device into a mouth of a patient, said reference surface device comprising:
      at least one sector including a length defining a first end of said at least one sector, a plurality of faces, each face of said plurality of faces at an angular orientation with respect to each adjacent face, the plurality of faces extending along the length of the at least one sector, the at least one sector including oppositely disposed edges which extend from the edges of the outermost faces to a second end of said at least one sector, and wherein said plurality of faces is configured to provide at least one fully intraoral reference surface operative to provide an identifiable positional characteristic; and,
      a mounting element in communication with said second end of said at least one sector, wherein said identifiable positional characteristic is at a predetermined three-dimensional spatial position from a mounting point adapted to be attached to a feature having a substantially fixed location relative to said intra-oral scene, said intra-oral scene being configured to provide information for determining the three-dimensional spatial position and orientation of a face on said reference surface device relative to the intra-oral scene;
   b) imaging the intra-oral scene and a plurality of faces thereby capturing a two-dimensional image of the intra-oral scene and at least one of said plurality of faces;
   c) processing said two-dimensional image to obtain a three-dimensional data set; and d) stitching said three-dimensional data set of said three dimensional scene with another data set of another three-dimensional scene including said reference surface device thereby determining said position of said intra-oral feature.

19. A method according to claim 18, wherein the imaging step comprises providing structured illumination.

20. A method according to claim 18, further comprising displaying structured illumination so as to provide said identifiable positional characteristic.

21. A method according to claim 20, wherein said imaging step further comprises providing a cursor over said intra-oral scene.

22. A method according to claim 21, further comprising locating said cursor over said intra-oral scene.

23. A method according to claim 18, further comprising, between step c) and step d) an additional step of identifying position and orientation indicia on at least one face of said plurality of faces in said intra-oral scene thereby determining a three-dimensional position of said mounting point as the position of the intra-oral feature.

24. A reference surface device for use with imaging of an intra-oral scene, the reference surface device comprising:
   a) at least one sector including a plurality of faces, each face of said plurality of faces at an angular orientation on said at least one sector, and wherein said plurality of faces is configured to provide at least one fully intraoral reference surface operative to provide an identifiable positional characteristic; and,
   b) a mounting element in communication with said at least one sector, wherein said identifiable positional characteristic is at a predetermined three-dimensional spatial position from a mounting point adapted to be attached to a feature having a substantially fixed location relative to said intra-oral scene, said intra-oral scene being configured to provide information for determining the three-dimensional spatial position and orientation of a face on said device relative to the intra-oral scene; and,
   wherein said device comprises at least one prism including said at least one sector, and wherein each face of said plurality of faces includes a pyramidal depression.

\* \* \* \* \*